United States Patent [19]

Spiegelberg et al.

[11] 4,252,238
[45] Feb. 24, 1981

[54] PACKAGE FOR A STACK OF REFRESHERS

[75] Inventors: Hans Spiegelberg, Täby, Sweden; Raimo Jämiä, Helsingfors, Finland

[73] Assignee: Salve S.A., Sodertalje, Sweden

[21] Appl. No.: 947,026

[22] Filed: Sep. 29, 1978

[30] Foreign Application Priority Data

Mar. 14, 1978 [SE] Sweden ............................ 7802883

[51] Int. Cl.³ .............................................. B65D 33/16
[52] U.S. Cl. ..................................... 206/210; 206/260; 206/274; 206/449; 229/62
[58] Field of Search ................. 229/62, 64; 206/210, 206/213, 260, 269, 265, 271, 449, 555, 274

[56] References Cited

U.S. PATENT DOCUMENTS

| 2,560,535 | 7/1951 | Allen | 206/260 X |
|---|---|---|---|
| 3,104,798 | 9/1963 | Stone | 229/62 |
| 3,295,744 | 1/1967 | Turpin et al. | 229/62 |
| 3,339,606 | 9/1967 | Kugler | 229/62 |
| 3,372,859 | 3/1968 | Bjorkengren et al. | 229/62 |
| 3,439,867 | 4/1969 | Paxton | 229/62 |
| 3,595,468 | 7/1971 | Repko | 229/62 |

FOREIGN PATENT DOCUMENTS 1112446  8/1961  Fed. Rep. of Germany ............ 229/62

Primary Examiner—Joseph M. Moy

[57] ABSTRACT

A package is disclosed for use in containing moisture containing refreshers, or other moisture containing material. The package is formed of a sheet material which embraces the moist material and defines a re-sealable flap extending from the package which defines the package opening. Initially the package is hermetically sealed.

23 Claims, 7 Drawing Figures

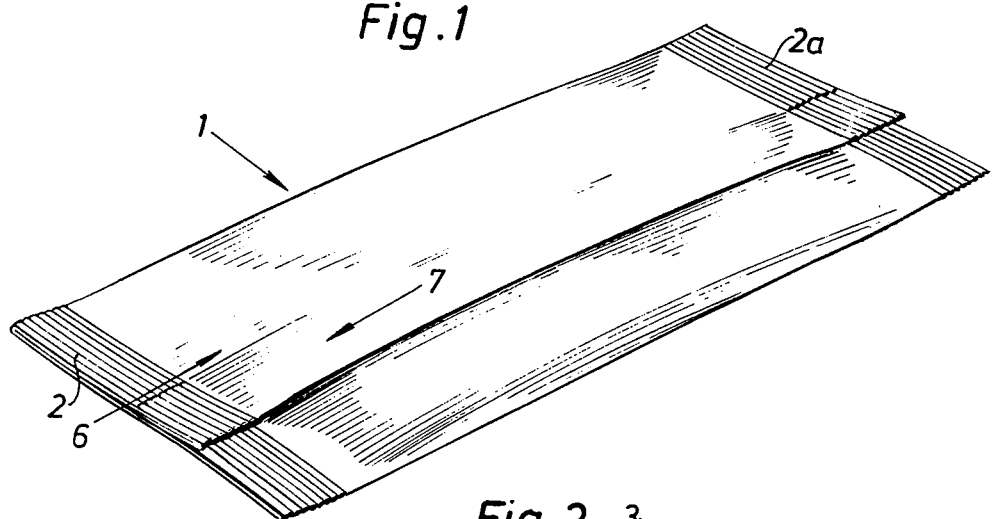
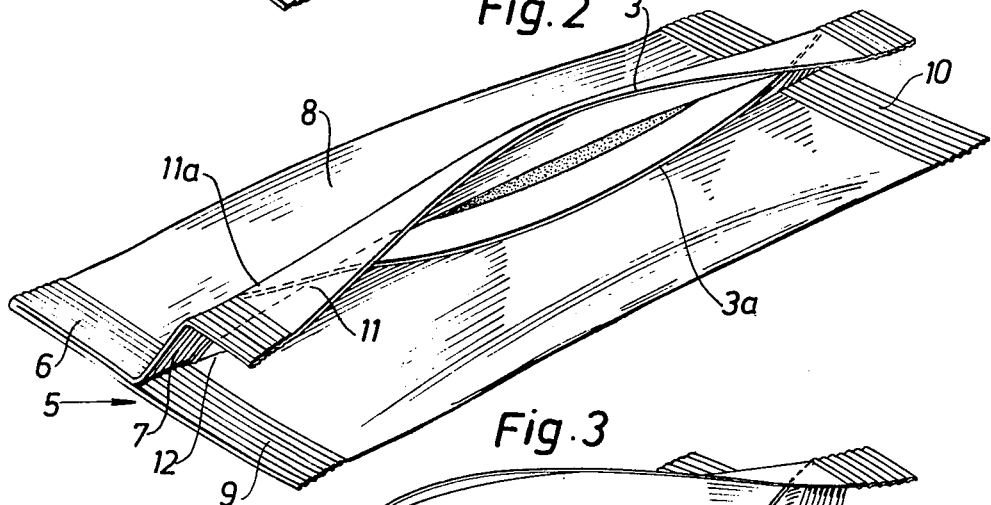
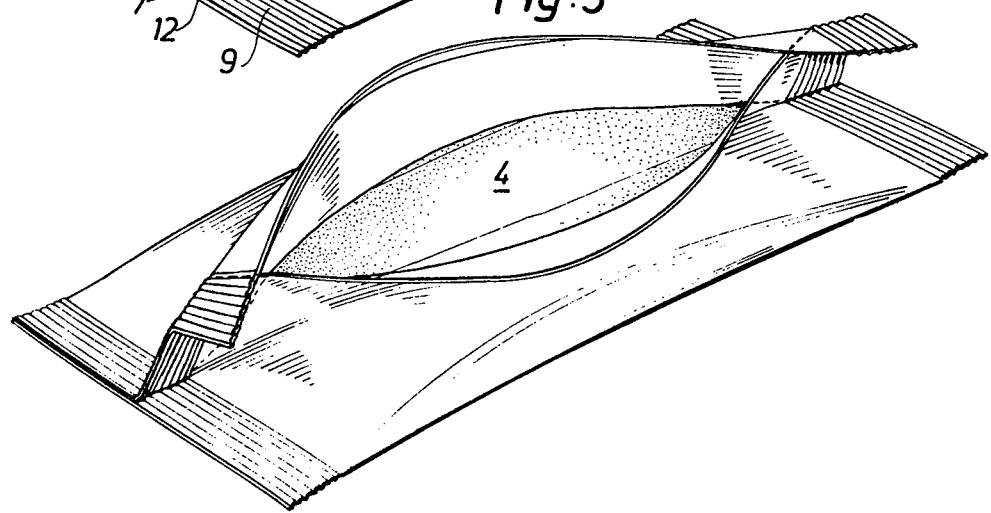

U.S. Patent  Feb. 24, 1981  Sheet 2 of 2  4,252,238
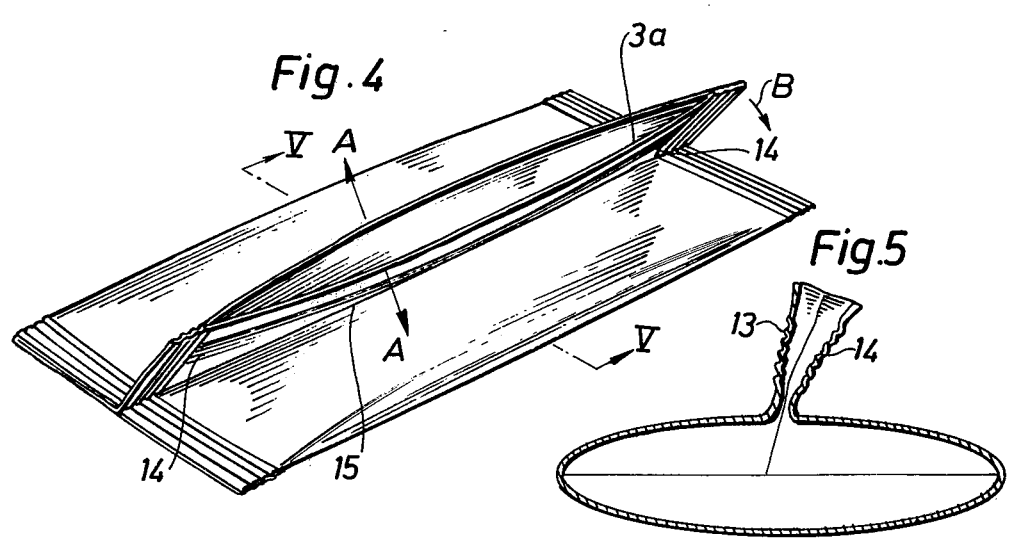
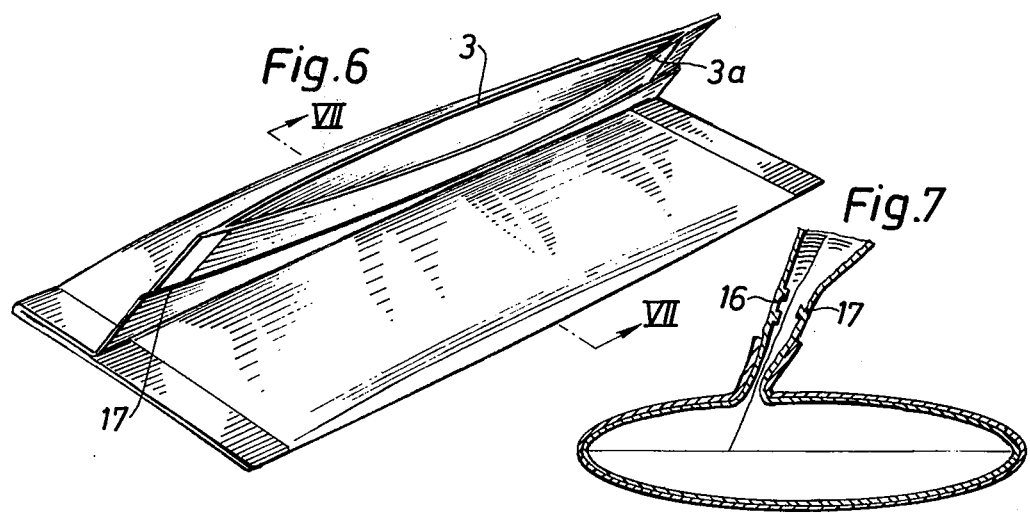

PACKAGE FOR A STACK OF REFRESHERS

BACKGROUND OF THE INVENTION

The present invention relates to a package, and more particularly to a re-sealable package suitable for containing a stack of refreshers or the like intended to be extracted individually, whilst the refreshers main in the package are prevented from drying out by re-sealing of the pack. However, a package in accordance with the invention may also be used to contain other materials which are to be kept in a damp condition until they are ready for use.

In this Specification the term "refresher" is used to mean an item for use in personal hygiene and when soap and water are unavailable and consisting of a sheet of, fabric, paper or non-woven material, for example, which is impregnated with a solution, such as, for example, a cleansing, antiseptic solution containing a mild cleansing component, a substrate replacing natural oil which prevents the skin from drying out, a bacteriocide and also, possibly a perfume. Such refreshers may be supplied in the form of a stack of individual sheets or a stack of sheets which are interconnected by perforated portions.

Such refreshers have been provided previously, and such previously provided refreshers have been packed individually in moisture impermeable wrappers of, for example, aluminium foil to retain the moisture within the refresher. Such wrapped refreshers have been marketed in a non-moisture-tight outer packages usually containing ten individually wrapped refreshers. If such a package is utilised each refresher is still moist at the time of use, but as each refresher has to be individually wrapped and since the non-moisture-tight outer package has to be provided, packaging costs are high, making the eventual purchase price high for the consumer.

In order to minimise the cost of a package of the refreshers it has also been proposed to provide a package for a stack of refreshers which are in direct contact with each other, the stack of refreshers being packaged in a moisture-impenetrable box which is provided with an opening in the upper surface of the box at the top of the box. A substantially tongue-shaped sealing member is provided, which also consists of a moisture-inpenetrable material, and the tongue-shaped sealing member is attached, by one end thereof to the upper surface of the box. The sealing member is of such length and width that it can cover the opening in the upper surface of the box and it is preferred that the tongue-shaped sealing member is formed at least partially of an easily deformable sealing material such as rubber. The sealing member is so designed that when the sealing member is in contact with the edges of the opening the deformable sealing material is brought into contact with the edges of the opening and the sealing member is sufficiently heavy to deform the sealing material so that a substantially moisture-tight seal is obtained. It will be appreciated that in utilizing such a package the opening can be exposed merely by lifting up the free end of the sealing member to permit one or more refreshers to be withdrawn from the package. Subsequently, when the sealing member is released, the opening in the package is automatically re-sealed. It will be appreciated that such a package is extremely bulky and is thus not suitable to replace the multiple pack described earlier in which the refreshers were individually wrapped, since the bulky package is inconvenient to carry in hand luggage on journeys, whilst the multiple pack is relatively small.

OBJECT OF THE INVENTION

The present invention seeks to provide a simple, re-sealable package for containing a plurality of refreshers or the like, or other material intended to be kept in a moist condition the package having a minimum bulk put permitting the withdrawl of refreshers or other material and being re-sealable to enable the refreshers or other material remaining in the package to retain their moisture until used.

SUMMARY OF THE INVENTION

According to this invention there is provided a re-sealable package for a stack or refreshers or other moist material wherein the package consists of a flexible, moisture impenetrable air-tight material which has been shaped to form a space for said material, two abutting portions of the said flexible material protruding from the space and being separable to form an opening through which material within the package may be withdrawn from the package, said abutting portions of the material initially hermetically sealing the package and being provided with means to re-seal the package when said hermetic seal has been broken.

Preferably the package comprises a first substantially rectangular foil and a second substantially rectangular assembly, said rectangular assembly being provided with the abutting portions of said material, the first foil and the assembly being joined to form said space.

Advantageously the package is formed from a substantially rectangular sheet of flexible moisture impenetrable and air-tight material, the sheet being folded around material to be contained within the package, end portions of the sheet abutting so that the sheet is folded to have a substantially "T" shaped configuration, the head of the "T" defining the space containing the material within the package and the abutting portions of the sheet forming the stem of the "T" protruding from the head thereof, the superimposed side edges of the sheet which have a substantially "T" shaped being hermetically sealed.

Preferably one of the abutting free end portions of the sheet is longer than the other so that the abutting sheets of the material forming the stem of "T" are of unequal length, the portion of longer length forming a flap which constitutes said re-sealing means and which can be folded around the free edge of the shorter portion of the sheet.

The said flap may be provided, at its base, with a stabilising weld, or with a longitudinal crease.

Alternatively the sealing means may comprise a first strip of elastically deformable material having longitudinal groove and a second strip of elastically deformable material having a longitudinal protrusion, said strips extending substantially opposite each other on said two abutting portions, the protrusion and groove being so shaped in relation to each other that after manual insertion of the protrusion into the groove a moisture-tight seal is formed.

Alternatively again sealing means comprise a plurality of grooves on the two abutting surfaces of the sheet material, the said grooves on the abutting surfaces being interengageable to form a substantially air tight seal.

The abutting portions of the sheet of material which form the stem of the "T" may be sealed together by means of a seal parallel with, but spaced from, the adjacent side edges of the sheet of material, said seal being easily torn open by pulling said side edges apart. The said seal may comprise an adhesive seal or welding seam joining the abutting surfaces of the sheet of material.

The bent superimposed side edges of the sheet may be sealed together by welding, or by means of adhesive.

Said sheet of material may comprise a laminate comprising a layer of metal and a layer of weldable thermoplastics material, and in particular a laminate comprising a bottom layer of polyester coated under vacuum with a thin layer of aluminium, the aluminium coated polyester being laminated to a layer of polythene.

BRIEF DESCRIPTION OF DRAWINGS

In order that the invention may be more readily understood, and so that further features thereof may be appreciated the invention will now be described by way of example with reference to the accompanying drawings in which:

FIG. 1 is a perspective view of one embodiment of a re-sealable package in accordance with the invention;

FIG. 2 corresponds to FIG. 1 but shows the package in a slightly opened state;

FIG. 3 corresponds to FIG. 1 but shows the package in a fully opened state;

FIG. 4 is a perspective view of a second embodiment of a re-sealable package in accordance with the invention, the package being illustrated in a slightly opened state;

FIG. 5 is a sectional view through the pack of FIG. 4 along the line V—V;

FIG. 6 is a perspective view of a further embodiment of a re-sealable package in accordance with the invention, the package being illustrated in a slightly opened state; and FIG. 7 is a sectional view through the package shown in FIG. 6 taken along the line VII—VII.

DESCRIPTION OF PREFERRED EMBODIMENTS.

Referring to FIGS. 1 to 3 a package in accordance with the invention consists of a sheet 1 of flexible, moisture-impenetrable and air tight material. Sheet 1 is of substantially rectangular shape and has four side edges 2, 2a and 3, 3a. The sheet 1 has been folded around a stack 4 of refreshers. The stack 4 is of rectangular configuration, the longer side of the stack of refreshers having a length which is slightly less than the width of the rectangular sheet 1. The width of the stack 4 of refreshers is equal to approximately one third of the length of the rectangular sheet 1. The stack of refreshers are located substantially centrally of the sheet 1, with the length of the stack 4 of refreshers extending across the width of the sheet 1. Subsequently the free ends of the sheet 1 are folded inwardly to embrace the stack of refreshers 4, the end portions of the free ends of the sheet 1 abutting one another and extending away from the sheet 4. Thus, the sheet 1 is formed to have, an end view, a substantially "T" shaped configuratin 5, the head section 6 of the "T" embracing the stack of refreshers within a space 8 and the stem section 7 of the "T" formed by the two end portions of the sheet 1 which abut one another protruding from the head section 6. The refreshers may be individual sheets located one on top of the other, but preferably the refreshers are folded in a "Z" shape and are arranged one on top of the other in such a way that a free end of each refresher is approximately in the middle of the opening that is formed in the package and that will be described hereinafter.

Superimposed side edge portions of the sheet 1 are hermetically sealed along the sealing edges 9, 10. Thus the sheet 1 is sealed, where it contacts itself, adjacent the narrow ends of the stack of refreshers 4.

As can be seen most clearly from FIGS. 2 and 3 the stack of refreshers are not located initially precisely in the centre of the sheet 1, but are offset slightly to one side, so that when the package has been formed the side edges 3, 3a of the abutting portions of the sheet 1 which form the stem 7 are not co-aligned, and thus a free flap 11 is formed which can be folded over the adjacent side edge 3a in order to re-seal the pack, once the pack has been opened. Preferably the flap 11 is provided, along its base with a narrow longitudinally stabilising weld 11a, so that the flap 11 has a tendency to assume its folded position, thus tending to re-seal the package. Alternatively a crease or the like may be used in place of the stabilising weld.

When the package is initially manufactured the package is hermetically sealed so that it is impossible for refreshers contained within the package to dry out at all before the package has been opened the preferred method of hermetically sealing the package is to provide one or more seals 12 which seal together the two abutting portions of the sheet of material 1 which form the stem portion 7 of the "T" configuration 5. One such seal can be provided along the base of the stem section 7, the seal effectively extending from one side edge 2 to the opposite side edge 2a of the sheet 1. This seal is indicated by the line 12. Of course, a seal may be provided at any appropriate point on the stem section 7. The seal must be broken when the package is opened.

FIG. 3 illustrates how the re-sealing flap 11 is opened for removal of one or more refreshers from the stack 4, the side edges 3 and 3a of the sheet 1 being pulled apart. When a refresher has been removed from the package in this way the side edges 3, 3a will return almost automatically to the position shown in FIG. 2, whereupon the flap 11 can simply be folded over the side edge 3a and the stem section 7 can again be bent down to lie adjacent the head section 6 as shown in FIG. 1. With the packaging in this condition the package is substantially re-sealed and it will be appreciated that the package can be re-sealed in a simple and efficient manner.

FIGS. 4 and 5 illustrate a second embodiment of the invention which generally resembles the embodiment as illustrated in FIG. 1, but in which the re-sealing means are not constituted by a fold-down flap 11, but instead are constituted by grooves 13 and 14 which are formed in the abutting portions of the sheet which form the stem of the "T". The grooves 13, 14 are spaced from the base of the stem "T" and can be pressed into each other to re-seal the package. As in the embodiment illustrated in FIG. 1 a package may be initially hermetically sealed by means of an additional weld extending either along the base of the stem section of the "T", as indicated by the line 15, or by means of some other easily torn weld close to the side edges 3, 3a.

The package illustrated in FIGS. 4 and 5 is opened in a manner corresponding to that described above with reference to FIGS. 1 to 3, in that the edges 3, 3a are pulled away from each other in the direction indicated by the arrows A and when a refresher has been removed from the package the side edges will return to almost the position shown in FIG. 4. The package can then be re-sealed merely be pressing the grooves 13, 14 into each other, and the stem 7 of the "T" can then be moved to lie adjacent the head 6 of "T". In order further to encourage the tendency of the stem section to be moved towards the head section in the direction of the arrow B upon the sealing, an appropriate crease may be provided at the base of the stem of the "T".

FIGS. 6 and 7 illustrate yet another embodiment of the invention, but it will be appreciated that this embodiment again generally corresponds with the embodiments described above. In this embodiment of the invention the abutting portions of the sheet that form the stem 7 of "T" shaped configuration are provided, respectively, with a first strip 16 of elastically deformable material having a longitudinal groove, and a second strip 17 of elastically deformable material having a longitudinal protrusion. The strips 16, 17 are located substantially opposite each other extending parallel to the side edges 3, 3a. The protrusion and groove are so designed that the protrusion may manually be pressed into the groove, the protrusion then being retained in the groove to provide a substantially air-tight seal. The protrusion can be manually separated from the groove by appropriately manipulating the free edges 3, 3a of the sheet of material forming the package.

Many materials may be used in forming a package in accordance with the invention as described above, but it is preferred to utilise a laminate. A typical laminate that can be utilised comprises a layer of metal such as aluminium which is laminated with a layer of weldable thermo-plastics material, such as polythene. If such a material is utilised in forming a package as described above, the weldable layer of thermoplastics material will be on the "inside" so that the faces of sheet material that are brought into abutment are the thermoplastics material faces of the sheet, thus permitting easy welding of the sheet. The nature of the laminate is shown in FIG. 6. Alternatively the sheet may be a laminate comprising a layer of polyester coated and a vacuum with a thin layer of aluminium, this polyester layer being laminated with a layer of polythene.

Whilst the invention has been described with reference to embodiments in which the abutting surfaces of the sheet are secured together by welding it is to be appreciated that the abutting surfaces of the sheet may be secured together by adhesive, both at the "T" shape side edges 2, 2a and to form the transverse seals extending across the stem 7 of the "T" configuration.

It is to be appreciated that a plurality of packages as described above may be located in a box or other non-moisture-impermeable container. Thus a person may buy a box or container of the packages and may remove one package from the box for insertion in a hand bag or pocket, the package containing sufficient refreshers for one day.

It is to be understood that the invention is not limited to the embodiments described above with reference to the accompanying drawings, but many alternative embodiments of the invention can be envisaged within the scope of the invention. For instance, instead of forming a package from a single rectangular sheet of material, the package can be formed from a lower sheet of material and a pre-produced upper assembly, the upper assembly comprising two sheets of foil joined together to form the stem of the "T" shaped section. The lower foil and the upper assembly can then be welded together along the four superimposed edges.

Whilst the package has been described as being of specific value in packaging moist articles such as refreshers a package in accordance with the present invention may be found to be of value for packaging other materials, such as tobacco or any other material which must be kept moist until use.

What is claimed is:

1. A re-sealable package for a stack of refreshers or other moist material comprising a sheet of flexible, moisture impenetrable air-tight material, said sheet being folded to form an inverted T-shaped container, the base of said inverted T-shaped container forming a substantially rectilinear space for the stack of refreshers, said folded sheet being hermetically sealed along all its end edges, the stem of the inverted T-shaped container comprising the free ends of said sheet forming two abutting portions protruding from the space and being separable to form an opening through which refreshers within the package may be withdrawn from the package, each said abutting portion of the material at the juncture of said stem and base portions being provided with a reinforced fold, said folds including initially hermetically sealing means to seal said package, said reinforced fold and said sealed end edges assisting said sealing means to re-seal the package when said hermetic seal has been broken, said reinforced fold extending from edge to edge and biasing said abutting portions in open and closed portions.

2. A resealable package according to claim 1 wherein said hermetically sealing means is a weld.

3. A resealable package according to claim 1 wherein said hermetically sealing means is a longitudinal crease.

4. A re-sealable package according to claim 1, wherein the abutting portions of the sheet of material which form the stem of the inverted T-shaped container are sealed together by means of a seal parallel with, but spaced from, the adjacent side edges of the sheet of material, said seal being easily torn open by pulling said side edges apart.

5. A re-sealable package according to claim 1 wherein one of the abutting free end portions of the sheet being longer than the other so that the abutting sheets of the material forming the stem of inverted T-shaped container are of unequal length, the portion of longer length forming a flap which constitutes resealing means and which can be folded around the free edge of the shorter portion of the sheet.

6. A re-sealable package according to claim 5 including a separable adhesive seal between the abutting free end portions.

7. A re-sealable package according to claim 5 including a separable welded seam joining the abutting free end portions.

8. A re-sealable package according to claim 1 wherein the sealing means comprise a first strip of elastically deformable material having longitudinal groove and a second strip of elastically deformable material having a longitudinal protrusion, said strips extending substantially opposite each other on said two abutting portions, the protrusion and groove being so shaped in relation to each other that after manual insertion of the protrusion into the groove a moisture-tight seal is formed.

9. A re-sealable package according to claim 5 wherein said sheet of material comprises a laminate comprising a layer of metal and a layer of weldable thermo-plastics material.

10. A re-sealable package according to claim 9 wherein the sheet of material comprises a laminate comprising a bottom layer of polyester coated under vacuum with a thin layer of aluminium, the aluminium coated polyester being laminated to a layer of polythene.

11. A re-sealable package according to claim 10, wherein said seal comprises an adhesive seal.

12. A re-sealable package according to claim 10, wherein said seal comprises a welding seam joining the abutting surfaces of the sheet of material.

13. A re-sealable package according to claim 8, wherein the abutting portions of the sheet of material which form the stem of the "T" are sealed together by means of a seal parallel with, but spaced from, the adjacent side edges of the sheet of material, said seal being easily torn open by pulling said side edges apart.

14. A re-sealable package according to claim 8, wherein the bent superimposed side edges of the sheet are sealed together by welding.

15. A re-sealable package according to claim 8, wherein the bent superimposed side edges of the sheet are sealed together by means of adhesive.

16. A re-sealable package according to claim 15, wherein said seal comprises an adhesive seal.

17. a re-sealable package according to claim 15 wherein said seal comprises a welding seam joining the abutting surfaces of the sheet of material.

18. A re-sealable package according to claim 1 wherein sealing means comprise a plurality of grooves on the two abutting surfaces of the sheet material, the said grooves on the abutting surfaces being interengageable to form a substantially air tight seal.

19. A re-sealable package according to claim 18, wherein the bent superimposed side edges of the sheet are sealed together by welding.

20. A re-sealable package according to claim 18, wherein the bent superimposed side edges of the sheet are sealed together by means of adhesive.

21. A re-sealable package according to claim 18, wherein the abutting portions of the sheet of material which form the stem of the "T" are sealed together by means of a seal parallel with, but spaced from, the adjacent side edges of the sheet of material, said seal being easily torn open by pulling said side edges apart.

22. A re-sealable package according to claim 1 wherein the end edges of the sheet are sealed together by welding.

23. In re-sealable package according to claim 1 wherein the end edges of the sheet are sealed together by means of adhesive.

* * * * *

UNITED STATES PATENT AND TRADEMARK OFFICE
CERTIFICATE OF CORRECTION

PATENT NO. : 4,252,238
DATED : February 24, 1981
INVENTOR(S) : Hans SPIEGELBERG and Raimo JAMIA It is certified that error appears in the above-identified patent and that said Letters Patent are hereby corrected as shown below:

On the cover sheet [73] should read:
--- Salve S. A., Geneve, Switerzerland ---.

Signed and Sealed this

Sixth Day of October 1981

[SEAL]

*Attest:*

*Attesting Officer*

GERALD J. MOSSINGHOFF

*Commissioner of Patents and Trademarks*